United States Patent [19]

Van Scott et al.

[11] 4,380,549

[45] * Apr. 19, 1983

[54] TOPICAL TREATMENT OF DRY SKIN

[76] Inventors: Eugene J. Van Scott, 1138 Sewell La., Rydal, Pa. 19046; Ruey J. Yu, 4 Lindenwold Ave., Ambler, Pa. 19002

[*] Notice: The portion of the term of this patent subsequent to Apr. 22, 1992, has been disclaimed.

[21] Appl. No.: 246,364

[22] Filed: Mar. 23, 1981

Related U.S. Application Data

[60] Continuation of Ser. No. 60,460, Jul. 25, 1979, abandoned, which is a continuation-in-part of Ser. No. 870,114, Jan. 17, 1978, Pat. No. 4,197,316, which is a division of Ser. No. 720,835, Sep. 7, 1976, Pat. No. 4,105,783, which is a continuation-in-part of Ser. No. 598,224, Jul. 23, 1975, Pat. No. 4,021,572.

[51] Int. Cl.$^3$ ............................................. A61K 31/19
[52] U.S. Cl. .................................... 424/317; 424/318
[58] Field of Search ................................ 424/317, 318

[56] References Cited

U.S. PATENT DOCUMENTS

| 2,118,566 | 5/1938 | Miles ................................ 424/317 X |
| 3,124,506 | 3/1964 | Holman ........................... 424/317 X |
| 3,666,863 | 5/1938 | Swanbeck ............................ 424/316 |
| 3,793,210 | 2/1974 | Corey ..................................... 252/89 |
| 3,879,537 | 4/1975 | Van Scott et al. ................... 424/311 |
| 4,021,572 | 5/1977 | Van Scott et al. ................... 424/317 |
| 4,105,783 | 8/1978 | Yu et al. .............................. 424/283 |

OTHER PUBLICATIONS

Harry–Modern Cosmeticology, vol. 1, pp. 417–434, (1955).
Sagarin–Cosmetics, Science & Technology, 1957, pp. 1066–1067.
Chemical Abstracts, (Taguchi et al.), vol. 79: 124905Z (1973).

Primary Examiner—Leonard Schenkman
Attorney, Agent, or Firm—LeBlanc, Nolan, Shur & Nies

[57] ABSTRACT

Preventive as well as therapeutic treatment to alleviate the symptoms of disorders characterized by cracking, flaking, or scaling of the skin consisting of the topical application of a solution, lotion, gel, stick, powder, cream or ointment containing as active ingredients one or more hydroxy acid or its analogue is disclosed. The hydroxyacid and its analogues include free acid, amide, lactone, ester, anhydride, organic or inorganic salt form of hydroxymonocarboxylic acids, hydroxydicarboxylic acids, hydroxytricarboxylic acids and keto acids. The therapeutic composition may include one or more of the compounds present in the total amount of from 0.1 to 20 percent. Topical application to affected areas has been found to ameliorate dry skin conditions.

12 Claims, No Drawings

TOPICAL TREATMENT OF DRY SKIN

This application is continuation of Ser. No. 060,460, filed July 25, 1979, now abandoned which is a continuation-in-part of our U.S. patent application Ser. No. 870,114, filed Jan. 17, 1978, now U.S. Pat. No. 4,197,316, which was a division of our U.S. patent application Ser. No. 720,835, filed Sept. 7, 1976, now U.S. Pat. No. 4,105,783, which in turn was a continuation-in-part of our patent application Ser. No. 598,224, filed July 23, 1975, now U.S. Pat. No. 4,021,572. This patent application is also related to our U.S. Pat. Nos. 4,105,782; 3,998,470; 3,984,566; 3,920,835; and 3,879,537. This application is also related to our U.S. patent application Ser. No. 948,489, filed Oct. 4, 1978, now U.S. Pat. No. 4,234,599.

In our patent application Ser. No. 870,114, filed Jan. 17, 1978, now U.S. Pat. No. 4,197,316, issued Apr. 8, 1980, the disclosure of which is hereby incorporated by reference, there is described the discovery that a reaction product of certain α-hydroxy acids and related compounds and certain organic amines or ammonium hydroxide are effective in the topical treatment of dry skin conditions.

Specifically, the acids and related compounds described were citric acid; glycolic acid; glucuronic acid; galacturonic acid; lactones, such as, glucuronolactone, and gluconolactone; α-hydroxybutyric acid; α-hydroxy-isobutyric acid; lactic acid; malic acid; mandelic acid; mucic acid; pyruvic acid; esters thereof, such as, methyl pyruvate and ethyl pyruvate; compounds related thereto, such as, β-phenyllactic acid and β-phenylpyruvic acid; β-hydroxybutyric acid; saccharic acid, tartaric acid; and tartronic acid.

Basic reactants described therein included ammonium hydroxide, organic primary, secondary or tertiary amines, such as, alkylamines, alkanolamines, diamines, dialkyl amines, dialkanolamines, alkylalkanolamines, trialkylamines, trialkanolamines, dialkylalkanolamines, and alkyl dialkanolamines wherein the alkyl or alkanol substitutent has from 1 to 8 carbon atoms.

Representative amines, as also described, were methylamine, ethylamine, monoethanolamine, monoisopropanol amine, ethylenediamine, 1,2-diaminopropane, dimethylamine, diethylamine, diethanolamine, diisopropanolamine, N-methylethanolamine, N-ethylethanolamine, triethylamine, triethanolamine, N-methyldiethanolamine, and triisopropylamine.

In our copending patent application Ser. No. 948,489, filed Oct. 4, 1978, the disclosure of which is hereby incorporated by reference, we describe our discovery that certain free acids, related compounds and reaction products with certain organic or inorganic bases were effective upon topical application to alleviate the symptoms of actinic and nonactinic keratoses.

Specifically, the free acids and related compounds described were citric acid; glycolic acid; glucuronic acid; gluconic acid; galacturonic acid; glucoheptonic acid; lactones, such as, glucoheptono 1,4 lactone, gluconolactone, glucuronolactone; α-hydroxybutyric acid; α-hydroxyisobutyric acid; α-hydroxyisocaproic acid; α-hydroxyisovaleric acid; lactic acid; atrolactic acid; malic acid; mandelic acid; mucic acid; pyruvic acid; esters thereof, such as, methyl pyruvate, ethyl pyruvate, and isopropyl pyruvate; saccharic acid; its lactone, saccharic acid 1,4-lactone; tartaric acid; tartronic acid; and related compounds, such as, β-hydroxybutyric acid; β-phenyllactic acid, β-phenylpyruvic acid.

This list of acids and related materials disclosed in our application Ser. No. 948,489, included the compounds identified application Ser. No. 870,114, and in additional gluconic acid, glucoheptonic acid, glucoheptono 1,4-lactone, α-hydroxyisocaproic acid, α-hydroxyisovaleric acid, atrolactic acid, isopropyl pyruvate, and saccharic 1,4-lactone. This list then totals twenty-nine related compounds found to be effective against skin keratoses.

The basic compounds enumerated as reactants also include the compounds listed in prior application Ser. No. 870,114, and additionally also included as a class quaternary amine compounds having from 1 to 8 carbon atoms. Specifically, the class includes basic choline.

It has now been discovered that the inventions described in our above identified Patents and patent applications have much broader therapeutic applicability. It has also been discovered that many additional related compounds as free acids, esters, lactones, amides and salts are of therapeutic value against a variety of skin keratinization disturbances and specifically useful in treating those disorders characterized generally as "dry skin".

This invention then relates to the treatment of skin disorders characterized by cracking, flaking or scaling of hands, feet or the body and genrally identified as "dry skin", and specifically, to compounds which have been found to be effective when topically applied to prevent as well as heal skin lesions associated with this condition in humans.

Severe "dry skin" conditions known as ichthyosis are hereditary disorders. The term ichthyosis alludes to a fish scale-like appearance of the human skin. Ichthyosis, characterized by a "dry skin" appearance, is usually detected during the early years of childhood. Small fine scales with a "pasted-on" appearance are found most prominently on the trunk and upper extremities. Larger, more adherent scales are present on the legs. Only a relatively small number of people are affected by this hereditary disorder.

In contrast to ichthyosis, mild to moderate "dry skin" conditions are quite common. Common "dry skin" conditions are specially pronounced during the fall and winter seasons, when environmental humidity is comparatively low. These conditions are characterized, in most instances, by the formation of fissures, chapping, cracking, or flaking of the skin on hands, face, neck and legs.

Conventional methods of treatment for all types of dry skin conditions primarily involve the topical application of oils or oil based preparations, and hydrating emollients. In addition, ointments containing salicylic acid, urea, glycerol, propylene glycol, sorbitol or vitamin A have been used. Prior treatments, however, have not been universally successful, and have, in many cases, been unable to promote healing to cause a complete remission of the symptoms. Because the mechanism responsible for causing dry skin conditions are not known, treatment has usually resulted in only temporary remission or healing of the flaky or scaly lesions.

We have not discovered that "dry skin" conditions may be successfully prevented or treated with the acid, amide, lactone, ester, anhydride, organic or inorganic salt form of certain hydroxy acids or their analogues.

In accordance with the present invention, the hydroxy acids and related compounds which are incorporated in therapeutic compositions for topical application to alleviate the symptoms of dry skin are of four classes:

| (A) Hydroxymonocarboxylic Acids | (B) Hydroxy-di and Tricarboxylic Acids |
|---|---|
| 1. Glycolic Acid | 1. Malic Acid |
| 2. Glucuronic Acid | 2. Mucic Acid |
| 3. Galacturonic Acid | 3. Citric Acid |
| 4. Gluconic Acid | 4. Saccharic Acid |
| 5. Glucoheptonic Acid | 5. Tartaric Acid |
| 6. α-Hydroxybutyric Acid | 6. Tartronic Acid |
| 7. α-Hydroxyisobutyric Acid | 7. Isocitric Acid |
| 8. α-Hydroxyisocaproic Acid | 8. Dihydroxymaleic Acid |
| 9. α-Hydroxyisovaleric Acid | 9. Dihydroxytartaric Acid |
| 10. β-Hydroxybutyric Acid | 10. Dihydroxyfumaric Acid |
| 11. Lactic Acid | |
| 12. β-Phenyllactic Acid | |
| 13. Atrolactic Acid | |
| 14. Mandelic Acid | |
| 15. Galactonic Acid | |
| 16. Pantoic Acid | |
| 17. Glyceric Acid | |

| (C) Ketoacids and Ketoesters | (D) Hydroxylactones |
|---|---|
| 1. Pyruvic Acid | 1. Gluconolactone |
| 2. Methyl Pyruvate | 2. Glucuronolactone |
| 3. Ethyl Pyruvate | 3. Glucoheptonolactone |
| 4. Isopropyl Pyruvate | 4. Galactonolactone |
| 5. Benzoylformic Acid | 5. Saccharic Acid lactone |
| 6. Methyl Benzoylformate | 6. Mucic Acid lactone |
| 7. Ethyl Benzoylformate | 7. Pantoyllactone |
| 8. β-Phenylpyruvic Acid | |
| 9. β-Hydroxypyruvic Acid | |
| 10. β-Hydroxypyruvic Acid Phosphate | |

The above hydroxyacids and related compounds may be used as free acids, lactones, esters, anhydrides or amides or salts formed by reacting the compound with ammonium hydroxide, organic or inorganic alkalis. In the case of hydroxy di-or tricarboxylic acids, Group B, several salts can be formed such as saccharic acid monopotassium salt or saccharic acid dipotassium salt. Citric acid may also form different salts as for example citric acid monoammonium salt, citric acid diammonium salt and citric acid triammonium salt.

It has been established through tests on humans having "dry skin" conditions that topical application of a solution, gel, powder, lotion, cream or ointment containing from about 0.1 to about 20 percent of at least one hydroxy acid, lactone, ester, amide, or ammonium salt or metallic salt of the present invention and preferably from about 0.2 to about 15 percent thereof, is therapeutically effective, when applied on a regular basis, to cause, within about one to two weeks, a return of the affected areas to a normal skin condition. If two or more hydroxy acids, lactones, esters, amides or ammonium or metallic salts are used in a composition of this invention, the total concentration of compounds is preferred not to exceed about 15 percent by weight of the composition. It has also been found in humans having frequent occurrence of cracking or flaking skin that topical application of a composition of this invention is effective, when applied on a regular basis, in preventing development or recurrence of skin lesions.

Accordingly, it is an object of this invention to provide a cosmetic composition containing at least one hydroxy acid, lactone, anhydride, ester, amide or ammonium or metallic salt, which when topically applied will prevent the development of dry skin conditions.

It is another object of this invention to provide a medicinal composition containing at least one hydroxy acid, lactone, anhydride, ester, amide and/or ammonium or metallic salt which when topically applied will substantially alleviate the symptoms of dry skin.

It is still another object to provide a method for treating dry skin with a nontoxic solution, gel, powder, lotion, cream or ointment of the present invention.

It is still another object to provide a safe and efficient method for treating the symptoms of dry skin through regular topical application of a medicinal composition which will promote healing within about one to two weeks.

It is yet another object of this invention to provide a method for formulating a cosmetic as well as medicinal composition in solution, gel, powder, lotion cream or ointment which when topically applied at least regularly to skin areas prone to lesions, cracking, flaking or scaling with prevent the development of dry skin or restore a normal healthy skin condition.

PREPARATION OF THE THERAPEUTIC COMPOSITIONS

Previously, in treatment of an extreme dry skin condition, such as ichthyosis, hydroxyacids, or ketoacids were prepared in a composition containing 5 to 20 percent by weight of the compound in a cream or ointment. The pH of such compositions was normally about 2 or less. In treatment of common dry skin conditions according to this invention we have discovered that compositions having a low pH cause some skin irritation (redness and sensation of burning) on sensitive subjects and are therefore not desirable. It is necessary then to develop compositions which are both therapeutically effective and not irritative. There are alternate ways for solving the above problem. One method is to lower the concentration of hydroxyacids used by, for example, utilizing a concentration of from 0.2 to 2% by weight of the total composition. Another method is to partially neutralize the hydroxyacid with ammonium hydroxide, or organic or inorganic alkalis to raise the pH of the composition from below 2 to a near 4 range. The optimal pH may range from 3.0 to 6.0.

As described in our previous patent application Ser. No. 720,835, filed Sept. 7, 1976, now U.S. Pat. No. 4,105,783, most inorganic alkalis will form inorganic salts with hydroxyacids which do not readily penetrate normal human skin. However, since normal human skin is usually slightly acidic (pH from 3.8 to 5.6), the inorganic salt of hydroxyacid may be partially converted to the free acid form when in contact with the human skin. Therefore, to some degree a percutaneous penetration of hydroxyacids in their inorganic salt form can be achieved.

Generally, a nontoxic composition of this invention should preferably have a pH of the solution, gel, lotion, cream or ointment between 3.0 and 6.0.

To prepare the composition of the present invention the hydroxyacid or its related compound is initially dissolved in water or ethanol. The initial concentration of the hydroxyacid or its related compound may range from 0.1 to 20 percent by weight of the total composition. The preferred concentration range, however, is from 0.2 to 15 percent. The solution thus prepared may then be admixed in a conventional manner with commonly available cream or ointment bases such as hydrophilic ointment.

A partially neutralized hydroxyacid composition may be prepared as follows: The aqueous or alcoholic solution of a hydroxyacid as prepared above is cooled externally with an ice-water bath. Ammonium hydroxide, organic or inorganic alkali is added to the solution until the pH ranges from 3.0 to 6.0. This slightly acidic solution is then admixed with oil-in-water or water-in-oil emulsion.

As disclosed in our prior patent applications, hydroxy acids of this invention may be partially neutralized as reaction products in aqueous or alcoholic solution with organic primary, secondary, tertiary or quaternary amines. These organic bases include alkylamines, alkanol amines, diamines, dialkylamines, dialkanolamines, alkylalkanolamines, trialkylamines, trialkanolamines, dialkylalkanolamines, and alkyl dialkanolamines having preferably alkyl or alkanol substituents with from 1 to 8 carbon atoms. Representative of such compounds were enumerated in our prior patent applications as described above.

As will be obvious to those skilled in the art, representative inorganic alkalis include ammonium, sodium and potassium hydroxide.

Certain amide, lactone, ester and partially neutralized forms of hydroxyacids are commercially available such as DL-lactamide, gluconolactone, ethyl pyruvate and saccharic acid monopotassium salt. These compounds may be dissolved in water or ethanol and then admixed with cosmetic or pharmaceutical emulsions.

The prophylactic as well as therapeutic composition may be prepared in a form of solution, gel, powder, stick, lotion, cream or ointment. In these instances, cosmetically acceptable ingredients are incorporated into the formulation, and lotions, creams or ointments are readily prepared.

The following are illustrative examples of formulations or compositions according to this invention. Although the examples utilize only selected formulations useful according to this invention, it should be understood that the following examples are illustrative and not limited. Therefore, any of the aforementioned acids, amides, lactones, anhydrides, esters or salts may be substituted according to the teachings of this invention in the following formulations.

EXAMPLE 1

The following is a typical example for formulating a free acid form of hydroxyacids which are primarily water soluble.

L-Tartaric acid 2 gm is dissolved in 2 ml of water, and the solution is admixed with 96 gm of hydrophilic ointment, U.S.P. Continue agitation until a uniform consistency is obtained. The pH of this cream is 2.4.

EXAMPLE 2

The following is a typical example for formulating a free acid form of hydroxyacids which are primarily lipid soluble.

DL-Mandelic acid 5 gm is dissolved in 10 ml of ethanol and the solution is admixed with 85 gm of hydrophilic ointment. U.S.P. Continue agitation until a uniform consistency is obtained. The pH of the composition is 2.7.

EXAMPLE 3

The following is a typical example for formulating an amide form of hydroxyacids which are primarily water soluble.

DL-Lactamide or glycolamide 10 gm is dissolved in 10 ml of water, and the solution is admixed with 80 gm of hydrophilic ointment, U.S.P. Continue agitation until a uniform consistency is obtained. The pH of the composition is 5.3.

EXAMPLE 4

The following is a typical example for formulating an amide form of hydroxyacids which are primarily lipid soluble.

DL-Mandelamide 10 gm is dissolved in 20 ml of ethanol, and the solution is admixed with 70 gm of hydrophilic ointment, U.S.P. Continue agitation until a uniform consistency is obtained. The pH of the composition is 5.7.

EXAMPLE 5

The following is a typical example for formulating an ester form of ketoacids which are primarily lipid soluble.

Ethyl pyruvate 5 ml is dissolved in 5 ml of ethanol, and the solution is admixed with 90 gm of hydrophilic ointment, U.S.P. Continue agitation until a uniform consistency is obtained. The pH of the composition is 5.6.

EXAMPLE 6

The following is a typical example for formulating a lactone form of hydroxyacids which are primarily water soluble.

D-Gluconic acid lactone or D-Saccharic acid-1,4-lactone 5 gm is dissolved in 10 ml of water, and the solution is admixed with 85 gm of hydrophilic ointment, U.S.P. Continue agitation until a uniform consistency is obtained. The pH of the composition is 2.8.

EXAMPLE 7

The following is a typical example for formulating an ammonium salt form of hydroxyacids which are primarily water soluble.

Citric acids 5 gm is dissolved in 10 ml of water, and concentrated ammonium hydroxide 2 ml is added to the solution. The solution is then admixed with 83 gm of hydrophilic ointment, U.S.P. Continue agitation until a uniform consistency is obtained. The pH of the cream is 3.5.

EXAMPLE 8

The following is a typical example for formulating an ammonium salt form of hydroxyacids which are primarily lipid soluble.

DL-Mandelic acid 5 gm is dissolved in 5 ml of ethanol, and water 8.4 ml and concentrated ammonium hydroxide 1.6 ml are added to the alcoholic solution. The whole solution is then admixed with 80 gm of hydrophilic ointment, U.S.P. Continue agitation until a uniform consistency is obtained. The pH of the cream is 4.2.

EXAMPLE 9

The following is a typical example for formulating a composition containing a monometallic salt of hydroxydicarboxylic acid.

D-Saccharic acid monopotassium salt 5 gm is dissolved in 10 ml of water and the solution is admixed with 85 gm of hydrophilic ointment, U.S.P. Continue agitation until a uniform consistency is obtained. The pH of the cream is 3.6.

EXAMPLE 10

The following is a typical example for formulating a composition containing a hydroxyacid partially neutralized with sodium hydroxide.

Glycolic acid 5 gm is dissolved in 5 ml of water and 4 N NaOH 10 ml is added to the solution. The solution is then admixed with 80 gm of hydrophilic ointment, U.S.P. Continue agitation until a uniform consistency is obtained. The pH of the cream is 4.2.

EXAMPLE 11

The following is a typical example for formulating a composition containing a hydroxyacid partially neutralized with potassium hydroxide.

DL-Mandelic acid 5 gm is dissolved in 5 ml of ethanol, and water 5 ml and 4 N KOH 5 ml are added to the alcoholic solution. The whole solution is then admixed with 80 gm of hydrophilic ointment, U.S.P. Continue agitation until a uniform consistency is obtained. The pH of the cream is 4.3.

EXAMPLE 12

The following is a typical example for formulating an oil-in-water emulsion containing an organic salt form of hydroxyacids.

| Part A: | |
| --- | --- |
| Polyoxyethylene (40) stearate | 3 gm. |
| Polyoxyethylene (20) sorbitan monooleate | 2 gm. |
| Glycerol Monostearate | 8 gm. |
| Lanolin | 2 gm. |
| Mineral oil | 1 gm. |
| Part B: | |
| Water | 49 ml. |
| Propylene glycol | 5 ml |
| Sorbitol | 3 gm |
| Carbomer 940 | 1 gm |

Heat both Part A and Part B to 80° C. Add Part B slowly to Part A with agitation. After the mixture is congealed add glycolic acid 10 gm and triisopropanolamine 16 gm. Continue agitation until a uniform consistency is obtained. The pH of the cream is 3.8.

EXAMPLE 13

The following is a typical example for formulating an oil-in-water emulsion containing an ammonium salt form of hydroxylactones.

| Part A: | |
| --- | --- |
| Polyoxyethylene (40) stearate | 3 gm |
| Polyoxyethylene (20) sorbitan monooleate | 2 gm |
| Glycerol monostearate | 4 gm |
| Cetyl alcohol | 3 gm |
| Beeswax | 3 gm |
| Mineral oil | 5 gm |
| Part B: | |
| Water | 59 ml |
| Propylene glycol | 5 ml |
| Sorbitol | 6 gm |
| Glycerol | 3 ml |
| Carbomer 940 | 0.5 gm |

Heat both Part A and Part B to 80° C. Add Part B slowly to Part A with agitation. After the mixture is congealed add gluconolactone 5 gm and concentrated ammonium hydroxide 1.2 ml. Continue agitation until a uniform consistency is obtained. The pH of the cream is 3.7.

EXAMPLE 14

The following is a typical example for formulating an oil-in-water emulsion containing an ammonium salt form of hydroxy acids.

| Part A: | |
| --- | --- |
| Polyoxyethylene (40) stearate | 2 gm |
| Polyoxyethylene (20) sorbitan monooleate | 1 gm |
| Glycerol monostearate | 5 gm |
| Cetyl alcohol | 3 gm |
| Beeswax | 3 gm |
| Mineral oil | 2 gm |
| Part B: | |
| Water | 71 ml |
| Propylene glycol | 5 ml |
| Carbomer 934 | 0.5 gm |

Heat both Part A and Part B to 80° C. Add Part B slowly to Part A with agitation. After the mixture is congealed add DL-mandelic acid 5 gm and concentrated ammonium hydroxide 1.7 ml. Continue agitation until a uniform consistency is obtained. The pH of the cream is 4.0.

EXAMPLE 15

The following is a typical example for formulating a water-in-oil emulsion containing a free acid form of hydroxyacids.

| Part A: | |
| --- | --- |
| Sorbitan sesquioleate | 10 gm |
| Petrolatum | 15 gm |
| Mineral oil | 15 gm |
| Beeswax | 15 gm |
| Isopropyl myristate | 15 gm |
| Part B: | |
| Water | 30 ml |
| Magnesium hydroxide | 2 mg |

Heat both Part A and Part B to 80° C. Add Part B slowly to Part A with agitation. After the mixture is congealed add 10% phosphoric acid 0.2 ml and DL-mandelic acid 0.2 gm. Continue agitation until a uniform consistency is obtained. The pH of this water-non-washable cream is 4.6.

EXAMPLE 16

The following is a typical example for formulating a water-in-oil emulsion containing an ester form of ketoacids.

| Part A: | |
| --- | --- |
| Sorbitan sesquioleate | 10 gm |
| Petrolatum | 15 gm |
| Mineral oil | 15 gm |
| Beeswax | 15 gm |
| Isopropyl myristate | 10 gm |

|  | Degree of Improvement | | | | |
|---|---|---|---|---|---|
|  | None (0) | Mid (1+) | Moderate (2+) | Substantial (3+) | Complete (4+) |
| THICKNESS | Highly elevated | Detectable reduction | Readily apparent reduction | Barely elevated | Normal thickness |
| TEXTURE | Visibly rough | Palpably rough | Uneven but not rough | Slightly uneven | Visibly and palpably smooth |

| Part B: | |
|---|---|
| Water | 23 ml |
| Propylene glycol | 5 ml |
| Sorbitol | 3 gm |
| Glycerol | 3 ml |
| Magnesium hydroxide | 0.1 gm |

Heat both Part A and Part B to 80° C. Add Part B slowly to Part A with agitation. After the mixture is congealed add 10% phosphoric acid 0.5 ml and aluminum phosphate 0.2 ml. Ethyl pyruvate 1 ml is then added to the cream. Continue agitation until a uniform consistency is obtained. The pH of this water-nonwashable cream is 5.6.

EXAMPLE 17

The following is a typical example for formulating a gel composition containing a free acid form of hydroxyacids.

DL-Mandelic acid 10 gm is dissolved in 50 ml of ethanol, and the alcoholic solution is admixed with 28.5 ml of water and 10 ml of propylene glycol. Hydroxypropylcellulose 1.5 gm is added to the mixture with agitation. Continue agitation until a uniform gel is formed. The pH of this gel is 2.7.

EXAMPLE 18

The following is a typical example for formulating a gel composition containing a hydroxylactone.

D-Gluconolactone 10 gm is dissolved in 79 ml of water, and the solution is admixed with 5 ml of ethanol and 5 ml of propylene glycol. Hydroxypropylcellulose 1 gm is added to the mixture with agitation. Continue agitation until a uniform gel is formed. The pH of this gel is 2.1.

EXAMPLE 19

The following is a typical example for formulating a powder composition containing a free acid form of hydroxyacids.

Citric acid 10 gm and Talc, U.S.P. grade 90 gm are admixed in a ball mill machine for an hour until a uniform consistency is obtained. The fine powder thus obtained is stored in powder cans with small holes on the caps.

TEST RESULTS (A) Severe Dry Skin

The involved skin in severe dry skin is hyperplastic (thickened) and has thick adherent scales. The degree of thickening is such that lesions are palpably and visually elevated. The thickened adherent scales cause the surface of involved skin to be markedly rough and uneven. These two attributes of thickness and texture can be quantified to allow objective measurement of degree of improvement from topically applied therapeutic test materials as follows:

By means of such parameters degrees of change in lesions can be numerically noted and comparisons made of one treated site to another.

In order to evaluate the hydroxyacids and their analogues of this invention a total of eight patients with severe dry skin conditions or ichthyosis were treated with the compositions as described in the Examples.

Treated areas were of a size convenient for topical applications, i.e., circles 4 cm in diameter demarcated with a plastic ring of that size inked on a stamp pad. The medicinal cream, gel or ointments were topically applied by the patient in an amount (usually about 0.1 cubic millimeter) sufficient to cover the treatment site. Applications were made three times daily and without occlusive dressings. Application periods did not exceed three weeks, and applications were discontinued at any time when resolution of the lesion on the treatment area was clinically judged to be complete. Clinical evaluations of degrees of improvement were made at intervals of daily to weekly.

The test results on patients with severe dry skin are summarized on the following tables.

TABLE 1

Topical effectiveness of hydroxyacids on severe dry skin

| Compounds | Number of Patients | Therapeutic effectiveness |
|---|---|---|
| 1. Glycolic acid | 8 | 4+ |
| 2. Glucuronic acid | 7 | 3+ |
| 3. Galacturonic acid | 7 | 3+ |
| 4. Gluconic acid | 8 | 4+ |
| 5. Glucoheptonic acid | 8 | 3+ |
| 6. Lactic acid | 8 | 4+ |
| 7. β-Phenyllactic acid | 8 | 3+ |
| 8. Atrolactic acid | 8 | 4+ |
| 9. α-Hydroxybutyric acid | 7 | 3+ |
| 10. Galactonic acid | 7 | 3+ |
| 11. α-Hydroxyisobutyric acid | 8 | 4+ |
| 12. Mandelic acid | 8 | 4+ |
| 13. Malic acid | 7 | 3+ |
| 14. Mucic acid | 7 | 3+ |
| 15. Citric Acid | 7 | 3+ |
| 16. Saccharic acid | 8 | 4+ |
| 17. Tartaric acid | 7 | 4+ |
| 18. Tartronic acid | 7 | 3+ |
| 19. β-Hydroxybutyric acid | 7 | 3+ |

TABLE 2

Topical effectiveness of ketoacids and esters thereof on severe dry skin

| Compounds | Number of Patients | Therapeutic effectiveness |
|---|---|---|
| 1. Pyruvic acid | 8 | 4+ |
| 2. Benzoylformic acid | 7 | 2+ |
| 3. β-Phenylpyruvic acid | 8 | 3+ |
| 4. Methyl Pyruvate | 8 | 3+ |
| 5. Ethyl Pyruvate | 8 | 3+ |
| 6. Isopropyl Pyruvate | 7 | 2+ |

TABLE 2-continued

Topical effectiveness of ketoacids and esters thereof on severe dry skin

| Compounds | Number of Patients | Therapeutic effectiveness |
|---|---|---|
| 7. Methyl Benzoylformate | 7 | 2+ |

TABLE 3

Topical effectiveness of hydroxylactones on severe dry skin

| Compounds | Number of Patients | Therapeutic effectiveness |
|---|---|---|
| 1. Gluconolactone | 8 | 4+ |
| 2. Gluconoheptonolactone | 6 | 2+ |
| 3. Glucuronolactone | 6 | 2+ |
| 4. Galactonolactone | 6 | 3+ |
| 5. Saccharic acid lactone | 6 | 3+ |
| 6. Pantoyl lactone | 5 | 2+ |

TABLE 4

Topical effectiveness of hydroxyamides and ketoamide on severe dry skin

| Compounds | Number of Patients | Therapeutic effectiveness |
|---|---|---|
| 1. Lactamide | 7 | 2+ |
| 2. Glycolamide | 6 | 2+ |
| 3. Mandelamide | 7 | 3+ |
| 4. Pyruvic Amide | 6 | 3+ |

TABLE 5

Topical effectiveness of ammonium and metallic salts of hydroxyacids on severe dry skin

| Compounds | Number of Patients | Therapeutic effectiveness |
|---|---|---|
| 1. Atrolactic acid ammonium salt | 6 | 2+ |
| 2. Saccharic acid mono-potassium salt | 7 | 3+ |
| 3. Tartaric acid mono-potassium salt | 6 | 2+ |

(B) Common Dry Skin

Human subjects with mild to moderate degrees of dry skin conditions, as evidenced by dry, cracking or flaking of the skin were instructed to apply topically the gel, lotion, cream or ointment of the present invention formulated according to Examples on the affected skin areas. Twice daily topical application was continued for a few weeks. In all the fifteen human subjects tested the feeling of the skin dryness disappeared after three to four days of topical treatment. In fifteen human subjects tested the rough and cracked skin usually became less pronounced within a week's time. Generally the skin appeared normal and felt smooth after about two weeks of topical treatment.

In contrast to the severe dry skin disease the common dry skin conditions once restored to normal appearing skin remained improved for some time until causes of dry skin, such as low humidity, cold weather, detergents, soaps, chemicals, etc., recurred. On continued use it was also found that twice daily topical application of a composition of the present invention prevented the development of new dry skin lesions.

The invention may be embodied in other specific forms without departing from the spirit of essential characteristics thereof. The present embodiment is, therefore, to be considered in all respects as illustrative and not restrictive, the scope of the invention being indicated by the appended claims and all changes which come within the meaning and range of equivalency of the claims are, therefore, intended to be embraced therein.

What is claimed is:

1. A method for alleviating the symptoms of dry skin in humans comprising topically applying to involved areas of the human body an effective amount of at least one member selected from the group consisting of:

| | |
|---|---|
| Glycolic Acid | Malic Acid |
| Glucuronic Acid | Mucic Acid |
| Galacturonic Acid | Citric Acid |
| Gluconic Acid | Saccharic Acid |
| Glucoheptonic Acid | Tartaric Acid |
| α-Hydroxybutyric Acid | Tartronic Acid |
| α-Hydroxyisobutyric Acid | Isocitric Acid |
| α-Hydroxyisocaproic Acid | Dihydroxymaleic Acid |
| α-Hydroxyisovaleric Acid | Dihydroxytartaric Acid |
| β-Hydroxybutyric Acid | Dihydroxyfumaric Acid |
| [Lactic Acid] | |
| β-Phenllactic Acid | |
| Atrolactic Acid | |
| Mandelic Acid | |
| Galactonic Acid | |
| Pantoic Acid | |
| Glyceric Acid | | or a salt thereof with an organic or inorganic alkali, in a pharmaceutically acceptable vehicle.

2. The method of claim 1 wherein said member is present in a concentration of from about 0.1 to 20 percent by weight.

3. The method of claim 1 wherein a plurality of said members are present in a total concentration of no more than about 15 percent by weight.

4. The method of claim 1 wherein said member is present as a salt with at least one base selected from the group consisting of ammonium hydroxide, sodium hydroxide and potassium hydroxide.

5. A method for alleviating the symptoms of dry skin in humans comprising topically applying an effective amount of at least one member selected from the group consisting of: pyruvic acid, benzoylformic acid, β-phenylpyruvic acid, β-hydroxypyruvic acid and β-hydroxypyruvic acid phosphate or a salt thereof with an organic or inorganic alkali, in a pharmaceutically acceptable vehicle.

6. The method of claim 5 wherein said member is present in a concentration of from about 0.1 to 20 percent by weight.

7. The method of claim 5 wherein a plurality of said members are present in a total concentration of no more than about 15 percent by weight.

8. The method of claim 5 wherein said member is present as a salt with at least one base selected from the group consisting of ammonium hydroxide, sodium hydroxide and potassium hydroxide.

9. A method for alleviating the symptoms of dry skin in humans comprising an effective amount of at least one member selected from the group consisting of: glyceric acid, gluconic acid, glucoheptonic acid, α-hydroxyisocaproic acid, α-hydroxyisovaleric acid, atrolactic acid, galatonic acid, isocitric acid, dihydroxymaleic acid, dehydroxytartaric acid, dihydroxyfumaric acid, benzoylformic acid, β-hydroxypyruvic acid, β-hydroxypyruvic acid phosphate, or a salt thereof with an organic or inorganic alkali in a pharmaceutically acceptable vehicle.

10. The method of claim 9 wherein said member is present in a concentration of from about 0.1 to 20 percent by weight.

11. The method of claim 9 wherein a plurality of said members are present in a total concentration of no more than about 15 percent by weight.

12. The method of claim 9 wherein said member is present as a salt with at least one base selected from the group consisting of ammonium hydroxide, sodium hydroxide and potassium hydroxide.

* * * * *

UNITED STATES PATENT AND TRADEMARK OFFICE
CERTIFICATE OF CORRECTION

PATENT NO. : 4,380,549

DATED : April 19, 1983

INVENTOR(S) : Van Scott et al

It is certified that error appears in the above-identified patent and that said Letters Patent is hereby corrected as shown below:

Col. 2, line 28, "genrally" should be --generally--;

Col. 2, line 63, "not" should be --now--;

Col. 4, line 21, "with" should be --will--;

Col. 12, line 20, delete brackets before and after "Lactic Acid".

Signed and Sealed this

Ninth Day of August 1983

[SEAL]

Attest:

Attesting Officer

GERALD J. MOSSINGHOFF

Commissioner of Patents and Trademarks